(12) United States Patent
Ishikawa et al.

(10) Patent No.: US 9,918,773 B2
(45) Date of Patent: Mar. 20, 2018

(54) PLASMA TREATMENT SYSTEM

(71) Applicant: OLYMPUS CORPORATION, Hachioji-shi, Tokyo (JP)

(72) Inventors: Manabu Ishikawa, Hachioji (JP); Shuichi Kimura, Hachioji (JP); Koichiro Watanabe, Higashiyamato (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/255,901

(22) Filed: Sep. 2, 2016

(65) Prior Publication Data
US 2016/0367307 A1    Dec. 22, 2016

Related U.S. Application Data (63) Continuation of application No. PCT/JP2015/059757, filed on Mar. 27, 2015.

(30) Foreign Application Priority Data

Apr. 11, 2014 (JP) ................. 2014-082288

(51) Int. Cl.
    *A61B 18/14* (2006.01)
    *A61B 18/04* (2006.01)
    *A61B 18/00* (2006.01)

(52) U.S. Cl.
    CPC ........ *A61B 18/042* (2013.01); *A61B 18/1402* (2013.01); *A61B 2018/00583* (2013.01);
    (Continued)

(58) Field of Classification Search
    CPC . A61B 18/042; A61B 18/1402; A61B 18/148; A61B 18/1482; A61B 18/1485;
    (Continued)

(56) References Cited

U.S. PATENT DOCUMENTS 5,683,366 A    11/1997  Eggers et al.
5,697,536 A    12/1997  Eggers et al.
(Continued)

FOREIGN PATENT DOCUMENTS

JP    H10-510745 A    10/1998
JP    H11-502144 A    2/1999
(Continued)

OTHER PUBLICATIONS

Dec. 15, 2015 Office Action issued in Japanese Patent Application No. 2015-545541.
(Continued)

*Primary Examiner* — Thomas Giuliani
(74) *Attorney, Agent, or Firm* — Oliff PLC (57) ABSTRACT

In a plasma treatment system, a temperature detection section detecting a temperature of a perfusion layer of an electrically conductive solution is fixed to a treatment portion, and is located at a position to be immersed in the perfusion layer when a first electrode portion and a second electrode portion are immersed in the perfusion layer. In the plasma treatment system, a control section controls an adjustment of a temperature in a temperature adjustment unit and controls a supply volume and a suction volume of the electrically conductive solution on the basis of a detection result in the temperature detection section so that the temperature of the perfusion layer is within a target temperature range.

12 Claims, 6 Drawing Sheets

(52) U.S. Cl.
CPC ............... *A61B 2018/00708* (2013.01); *A61B 2018/00714* (2013.01); *A61B 2018/00744* (2013.01); *A61B 2018/00779* (2013.01); *A61B 2018/00791* (2013.01); *A61B 2018/00863* (2013.01)

(58) Field of Classification Search
CPC ........ A61B 18/1487; A61B 2018/1472; A61B 2018/00583; A61B 2018/00791; A61B 2018/00779; A61B 2018/00744; A61B 2018/00714; A61B 2018/00708; A61B 2018/00863
USPC .................................. 606/34, 38, 41, 42, 50
See application file for complete search history.

(56) References Cited

U.S. PATENT DOCUMENTS

| | | |
|---|---|---|
| 7,387,625 B2 | 6/2008 | Hovda et al. |
| 2006/0241577 A1 | 10/2006 | Balbierz et al. |
| 2006/0253117 A1 | 11/2006 | Hovda et al. |
| 2011/0118601 A1 | 5/2011 | Barnes et al. |
| 2011/0270242 A1* | 11/2011 | Marion ................ A61B 18/148 606/35 |
| 2013/0116682 A1 | 5/2013 | Koo et al. |

FOREIGN PATENT DOCUMENTS

| | | |
|---|---|---|
| JP | 2003-528684 A | 9/2003 |
| JP | 2011-045756 A | 3/2011 |
| JP | 2013-099534 A | 5/2013 |
| WO | 99/30655 A1 | 6/1999 |

OTHER PUBLICATIONS

Jun. 23, 2015 Search Report issued in International Patent Application No. PCT/JP2015/059757.

Oct. 12, 2016 International Preliminary Report on Patentability issued in International Application No. PCT/JP2015/059757.

Nov. 7, 2017 Extended European Search Report and search opinion issued in European Patent Application No. 15776131.3.

\* cited by examiner

PLASMA TREATMENT SYSTEM

CROSS-REFERENCE TO RELATED APPLICATIONS

This is a Continuation application of PCT Application No. PCT/JP2015/059757, filed Mar. 27, 2015 and based upon and claiming the benefit of priority from prior Japanese Patent Application No. 2014-082288, filed Apr. 11, 2014, the entire contents of which are incorporated herein by reference.

BACKGROUND OF THE INVENTION

1. Field of the Invention

The present invention relates to a plasma treatment system which generates plasma in a perfusion layer of an electrically conductive solution by the passage of a radio-frequency current through the perfusion layer across a first electrode portion and a second electrode portion that are provided in a treatment portion, and uses the generated plasma to treat a treated target.

2. Description of the Related Art

Jpn. Pat. Appln. KOKAI Publication No. 2011-45756 has disclosed a plasma treatment system including a treatment instrument in which a first electrode portion (active electrode) and a second electrode portion (return electrode) are provided in a treatment portion of a probe. In this plasma treatment system, the first electrode portion is provided in a state where the position thereof relative to the second electrode portion does not change. The treatment instrument is provided with a sheath through which a probe is inserted in a state where the treatment portion protrudes toward the distal direction. A supply path is formed between the sheath and the probe, and a spout of the supply path is formed at the distal end of the sheath. A suction path is formed inside the probe, and a suction hole of the suction path is formed on the distal surface of the treatment portion. In a treatment, an electrically conductive solution (physiological saline) is supplied through the supply path, and the supplied electrically conductive solution is sucked through the suction path. Consequently, in the treatment, a perfusion layer of the electrically conductive solution from the spout of the supply path toward the suction hole of the suction path is formed between a treated target and the treatment portion.

By the transmission of radio-frequency energy (radio-frequency electric power) to the first electrode portion and the second electrode portion in a state where the first electrode portion and the second electrode portion are immersed in the perfusion layer, a radio-frequency current flows between the first electrode portion and the second electrode portion in the perfusion layer. If a voltage between the first electrode portion and the second electrode portion is increased, the radio-frequency current flows through the perfusion layer of the electrically conductive solution, and a vapor layer is thereby formed between the first electrode portion and the second electrode portion of the perfusion layer. Further, a breakdown occurs in the vapor layer, and plasma is generated in the perfusion layer of the electrically conductive solution. In the treatment, a treated target such as a living tissue is ablated by the generated plasma. Such a treatment is referred to as a low-temperature ablation treatment, and is used in, for example, the resection of a tonsil. The control of the radio-frequency energy transmitted to the first electrode portion and the second electrode portion and others are performed by a plasma treatment control unit.

BRIEF SUMMARY OF THE INVENTION

According to one aspect of the invention, a plasma treatment system includes that: a supply path in which a spout configured to spout an electrically conductive solution is formed, and which is configured to supply the electrically conductive solution toward the spout; a suction path in which a suction hole configured to suck the electrically conductive solution is formed, and which is configured to suck the electrically conductive solution to form a perfusion layer of the electrically conductive solution from the spout toward the suction hole; a treatment portion including a first electrode portion and a second electrode portion which is provided in a state where a position thereof relative to the first electrode portion does not change, the treatment portion being configured to generate plasma in the perfusion layer by a supply of radio-frequency energy to the first electrode portion and the second electrode portion in a state of immersing these electrode portions in the perfusion layer, thereby treating a treated target; a temperature adjustment unit which is configured to adjust a temperature of the electrically conductive solution before the spout of the electrically conductive solution from the spout; a temperature detection section which is fixed to the treatment portion, and which is located at a position to be immersed in the perfusion layer in a state where the first electrode portion and the second electrode portion are immersed in the perfusion layer, whereby a temperature of the perfusion layer is detected in a state of immersing the electrode portions in the perfusion layer; and a control section which is configured to control an adjustment of the temperature of the electrically conductive solution in the temperature adjustment unit and control a supply volume of the electrically conductive solution supplied through the supply path and a suction volume of the electrically conductive solution sucked through the suction path on the basis of a detection result in the temperature detection section so that the temperature of the perfusion layer is within a target temperature range.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

A first embodiment of the present invention is described with reference to FIG. 1 to FIG. 6.

Figure 1:
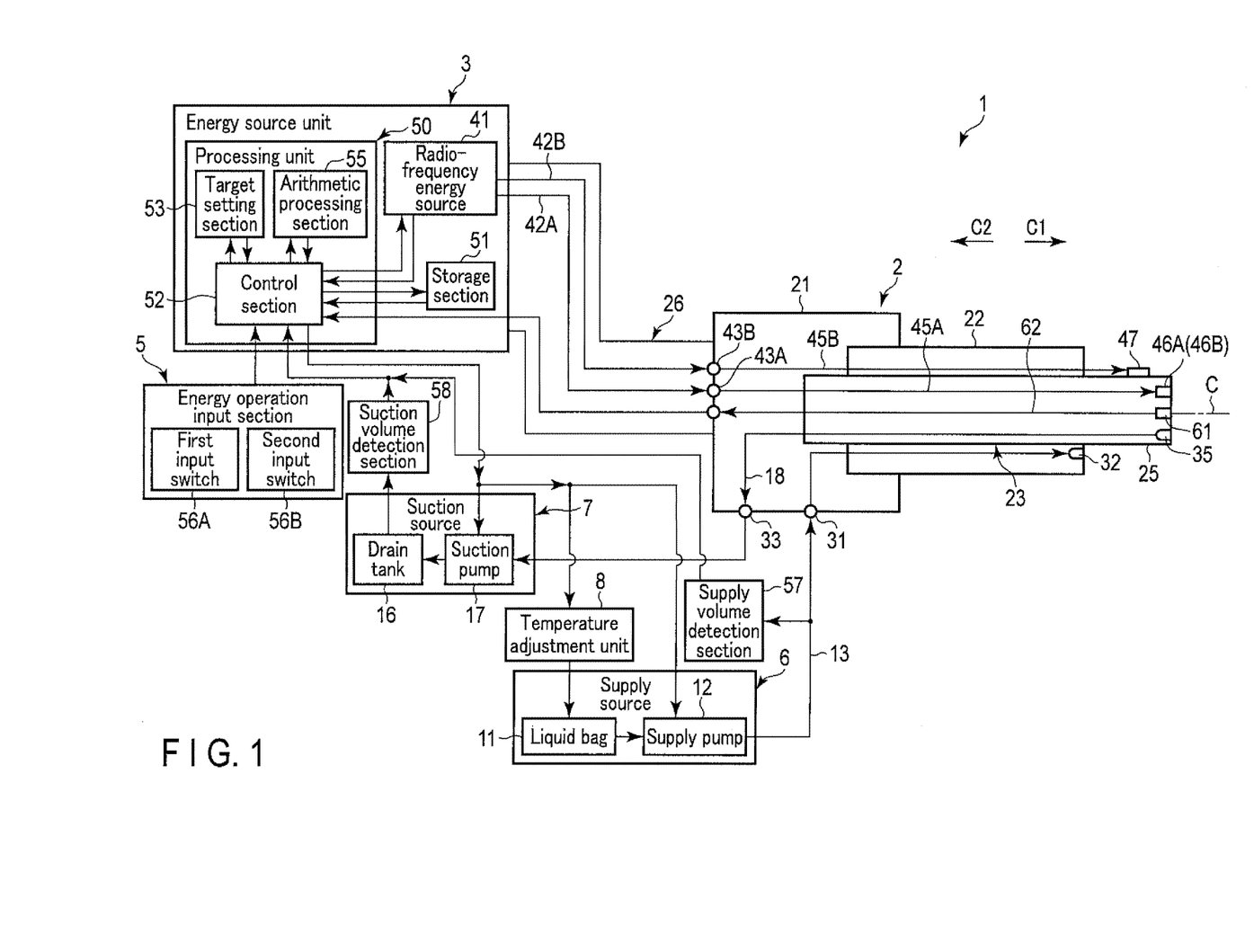
FIG. 1 is a schematic diagram showing a plasma treatment system according to a first embodiment.

FIG. 1 is a diagram showing a plasma treatment system 1 according to the present embodiment. This plasma treatment system 1 is used in a treatment to generate plasma, and ablate a living tissue which is a treated target by this plasma. As a result of the resection of the living tissue using the plasma, heat damage to the periphery of the resected tissue is relatively reduced, and a minimally invasive treatment is achieved. The plasma treatment system 1 is used, for example, in the field of otolaryngology for the resection of tonsillar tissue. This plasma treatment system 1 may also be used, for example, in the field of orthopedics for synovectomy or chondrectomy, or may also be used in abdominal surgery in general for the resection of organs (a liver in particular).

As shown in FIG. 1, the plasma treatment system 1 comprises a treatment instrument (plasma treatment instrument) 2. This treatment instrument 2 has a longitudinal axis C. Here, one of two directions parallel to the longitudinal axis C is a distal direction (direction of an arrow C1 in FIG. 1), and the direction opposite to the distal direction is a proximal direction (direction of an arrow C2 in FIG. 1). The plasma treatment system 1 includes an energy source unit 3 such as an energy generator, and an energy operation input section 5 such as a foot switch. A supply source (liquid supply source) 6 and a suction source 7 are provided in the plasma treatment system 1. A temperature adjustment unit 8 such as a temperature adjustment heater is provided in the plasma treatment system 1.

The supply source 6 includes a liquid bag 11 such as a physiological saline bag, and a supply pump (liquid supply pump) 12. The liquid bag 11 is filled with an electrically conductive solution such as a physiological saline. One end of a supply path (liquid supply path) 13 is connected to the supply source 6. The supply path 13 is formed by, for example, an external supply tube (not shown) outside the treatment instrument 2. The electrically conductive solution (liquid) filling the liquid bag 11 is supplied through the supply path 13 by the actuation of the supply pump 12.

The suction source 7 includes a drain tank 16 and a suction pump 17. One end of a suction path 18 is connected to the suction source 7. The suction path 18 is formed by, for example, an external suction tube (not shown) outside the treatment instrument 2. A suctioned object such as a drain is sucked through the suction path 18 by the actuation of the suction pump 17, and collected in the drain tank 16.

The treatment instrument (plasma treatment instrument) 2 includes a holding case (holding portion) 21 which is held by a surgeon, a sheath 22 coupled to the distal direction side of the holding case 21, and a probe 23 which is inserted through the sheath 22. The probe 23 and the sheath 22 are inserted in the holding case 21 from the distal direction side. A treatment portion 25 is formed in the distal portion of the probe 23. The treatment portion 25 protrudes from the distal end of the sheath 22 toward the distal direction. One end of a cable 26 is removably connected to the holding case 21. The other end of the cable 26 is connected to the energy source unit 3.

Figure 2:
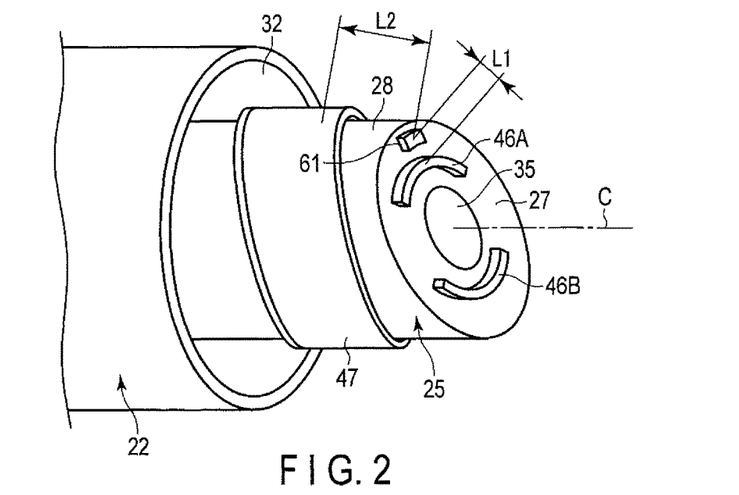
FIG. 2 is a perspective view schematically showing the configurations of the distal portion of a sheath and a treatment portion of a probe according to the first embodiment.

FIG. 2 is a diagram showing the configurations of the distal portion of the sheath 22 and the treatment portion 25 of the probe 23. As shown in FIG. 2, the treatment portion 25 protrudes from the sheath 22 toward the distal direction, and is exposed to the outside. The treatment portion 25 includes a distal surface 27 forming the distal end of the probe 23, and an outer circumferential surface 28 forming the outer circumference of the treatment portion 25.

As shown in FIG. 1, a supply port (liquid supply port) 31 is formed in the holding case 21. The supply path 13 is inserted into the holding case 21 from the supply port 31. In the present embodiment, the supply path 13 extends through the space between the probe 23 and the sheath 22. In the treatment instrument 2, the supply path 13 is formed by, for example, the supply tube (not shown) extending between the probe 23 and the sheath 22. The supply path 13 is separable in the supply port 31. As shown in FIG. 2, a spout 32 of the supply path 13 is formed in the treatment portion 25. In the present embodiment, the spout 32 is located at the distal end of the space between the sheath 22 and the probe 23, and is open toward the distal direction. The electrically conductive solution supplied through the supply path 13 spouts to the outside of the treatment instrument 2 (the outside of the sheath 22) from the spout 32 toward the distal direction.

As shown in FIG. 1, a suction port 33 is formed in the holding case 21. The suction path 18 is inserted into the holding case 21 from the suction port 33. In the present embodiment, the suction path 18 extends through an inside of the probe 23. In the treatment instrument 2, the suction path 18 is formed by, for example, the suction tube (not shown) extending inside the probe 23. The suction path 18 is separable in the suction port 33. As shown in FIG. 2, a suction hole 35 of the suction path 18 is formed in the treatment portion 25. In the present embodiment, the suction hole 35 is located on the distal surface 27 of the treatment portion 25, and is open toward the distal direction. The electrically conductive solution or the like that has been ejected from the spout 32 is sucked from the suction hole 35 as the suctioned object. The suctioned object is then suctioned from the outside of the treatment instrument 2 through the suction hole 35 and the suction path 18, and collected in the drain tank 16.

In the present embodiment, the cable 26 is attachable to and detachable from the holding case 21 of the treatment instrument 2. The supply path 13 is separable in the supply port 31 of the holding case 21, and the suction path 18 is separable in the suction port 33 of the holding case 21. Thus, after the use of the treatment instrument 2, the treatment instrument 2 can be separated from the energy source unit 3 (the cable 26), the energy operation input section 5, the supply source 6, and the suction source 7. As a result, it is possible to dispose of the treatment instrument 2 alone, and reuse equipment (e.g., the energy source unit 3 and the energy operation input section 5) other than the treatment instrument 2.

The energy source unit 3 includes a radio-frequency energy source 41 which is configured to output radio-frequency energy (radio-frequency electric power). The radio-frequency energy source 41 is, for example, an electric power supply (alternating electric power supply) provided in the energy generator, and outputs radio-frequency electric power such that the waveform of the radio-frequency current may be, for example, a sinusoidal wave or a triangular wave. One end of a first external radio-frequency path 42A and one end of a second external radio-frequency path 42B are connected to the high-frequency energy source 41. The first external radio-frequency path 42A and the second external radio-frequency path 42B extend through an inside of the cable 26. The first external radio-frequency path 42A and the second external radio-frequency path 42B are formed by, for example, electric wires (not shown) extending inside the cable 26. The first external radio-frequency path 42A and the second external radio-frequency path 42B are electrically insulated from each other.

A first connection terminal 43A and a second connection terminal 43B are provided in the holding case 21 of the treatment instrument 2. The first connection terminal 43A and the second connection terminal 43B are electrically insulated from each other. One end (proximal end) of a first internal radio-frequency path 45A is connected to the first connection terminal 43A, and one end (proximal end) of a second internal radio-frequency path 45B is connected to the second connection terminal 43B. The first internal radio-frequency path 45A and the second internal radio-frequency path 45B extend through the treatment instrument 2, and are electrically insulated from each other. The first internal radio-frequency path 45A is formed by, for example, an electric wire (not shown) extending inside the probe 23 and an electrically conductive portion (not shown) of the probe 23. The second internal radio-frequency path 45B is formed by, for example, an electric wire (not shown) extending in the space between the probe 23 and the sheath 22, and an electrically conductive portion (not shown) of the sheath 22. If the cable 26 is connected to the holding case 21, the first external radio-frequency path 42A is electrically connected to the first internal radio-frequency path 45A in the first connection terminal 43A, and the second external radio-frequency path 42B is electrically connected to the second internal radio-frequency path 45B in the second connection terminal 43B.

As shown in FIG. 2, two first electrode portions (active electrodes) 46A and 46B are fixed to the distal surface 27 of the treatment portion 25 in the present embodiment. The first electrode portions 46A and 46B are made of an electrically conductive material, and are located on the outer circumferential side with respect to the suction hole 35 of the suction path 18 in the present embodiment. The first electrode portions 46A and 46B are disposed apart from each other around the longitudinal axis. As shown in FIG. 1, the other end (distal end) of the first internal radio-frequency path 45A is connected to the first electrode portions 46A and 46B. The first electrode portions 46A and 46B function as electrodes by the supply of radio-frequency energy from the radio-frequency energy source 41 through the first external radio-frequency path 42A and the first internal radio-frequency path 45A.

As shown in FIG. 2, one second electrode portion (return electrode) 47 is fixed to the outer circumferential surface 28 of the treatment portion 25 in the present embodiment. The second electrode portion 47 is made of an electrically conductive material, and extends in a range of whole circumference of the outer circumferential surface 28 around the longitudinal axis in the present embodiment. The second electrode portion 47 is located on the distal direction side with respect to the distal end (the spout 32) of the sheath 22. Here, the first electrode portions 46A and 46B and the second electrode portion 47 are fixed to the treatment portion 25. Thus, the first electrode portions 46A and 46B and the second electrode portion 47 are provided in the treatment portion 25 in a state where their positions relative to each other do not change. The first electrode portions 46A and 46B and the second electrode portion 47 are located between the spout 32 of the supply path 13 and the suction hole 35 of the suction path 18. As shown in FIG. 1, the other end (distal end) of the second internal radio-frequency path 45B is connected to the second electrode portion 47. The second electrode portion 47 functions as an electrode different from the first electrode portions 46A and 46B by the supply of high-frequency energy from the radio-frequency energy source 41 through the second external radio-frequency path 42B and the second internal radio-frequency path 45B. That is, the second electrode portion 47 functions as an electrode different in electric potential from the first electrode portions 46A and 46B.

The energy source unit 3 includes a processing unit (processor) 50 including, for example, a central processing unit (CPU) and an application specific integrated circuit (ASIC), and a storage section 51 such as a memory. The processing unit 50 is electrically connected to the radio-frequency energy source 41 and the storage section 51, and the processing unit 50 is configured to transmit a control signal and others to the radio-frequency energy source 41. The processing unit 50 includes a control section 52, a target setting section 53, and an arithmetic processing section 55. The control section 52, the target setting section 53, and the arithmetic processing section 55 are, for example, parts (e.g., a control circuit and an arithmetic circuit) of an electronic circuit constituting the CPU and the ASIC. The control section 52, the target setting section 53, and the arithmetic processing section 55 are electrically connected to one another, and are configured to transmit electric signals and others to one another. Although the processing unit 50 and the storage section 51 are provided integrally with the radio-frequency energy source 41 in the present embodiment, the processing unit 50 and the storage section 51 may be provided separately from the radio-frequency energy source 41 in a certain modification. Further, processing in the storage section 51, the control section 52, the target setting section 53, and the arithmetic processing section 55 will be described in detail later.

An energy operation to output radio-frequency energy from the radio-frequency energy source 41 is input in the energy operation input section 5, for example, a foot switch. An operation signal is transmitted to the control section 52 from the energy operation input section 5 in a wired or wireless manner on the basis of the input of the energy operation. On the basis of the operation signal (the input of the energy operation), the control section 52 controls the output state of the radio-frequency energy from the radio-frequency energy source 41. The output state including, for example, a current value and a voltage value of the radio-frequency energy from the radio-frequency energy source 41 is detected, and information such as the detected current value is transmitted to the control section 52 of the processing unit 50. For example, a first input switch 56A and a second input switch 56B are provided in the energy operation input section 5. If the first input switch 56A is turned on, radio-frequency energy is output from the radio-frequency energy source 41 in an ablation output mode used in a treatment to ablate a treated target such as a living tissue. If the second input switch 56B is turned on, radio-frequency energy is output from the radio-frequency energy source 41 in a coagulation output mode used in a treatment to coagulate the treated target. Generally, a voltage between the first electrode portions 46A and 46B and the second electrode portion 47 is higher in the ablation output mode than in the coagulation output mode.

In a certain example, an energy level adjustment section (not shown) may be provided in the energy operation input section 5 so that the surgeon can adjust the energy level of the radio-frequency energy output from the high-frequency energy source 41 in each of the ablation output mode and the coagulation output mode. A memory (not shown) to store an identification number (ID) may be provided in the treatment instrument 2 so that the control section 52 of the processing unit 50 reads the ID of the treatment instrument 2 to which the cable 26 is connected by the connection of the cable 26 to the holding case 21. In this configuration, the storage section 51 stores ID information regarding more than one kind of treatment instrument 2 different in specifications (e.g., the dimensions, positions, shapes of the active electrodes and the return electrode, and the dimensions of the supply path), and information regarding the energy level of the radio-frequency energy corresponding to each ID. On the basis of the read ID and the information stored in the storage section 51, the energy level of the radio-frequency energy output from the radio-frequency energy source 41 in each of the ablation output mode and the coagulation output mode is automatically set.

The control section 52 of the processing unit 50 is configured to transmit control signals to the supply pump 12 of the supply source 6 and to the suction pump 17 of the suction source 7 in a wired or wireless manner, and configured to control the actuation state of the supply pump 12 and the actuation state of the suction pump 17. The supply volume (liquid supply volume) of the electrically conductive solution from the supply source 6 changes in accordance with the change of the actuation state of the supply pump 12. The suction volume of the sucked object (electrically conductive solution) by the suction source 7 changes in accordance with the change of the actuation state of the suction pump 17. A supply volume detection section (liquid supply volume detection section) 57 is disposed in the supply path 13. In the present embodiment, the supply volume detection section 57 is located outside the treatment instrument 2. The supply volume detection section 57 is, for example, one of known flow volume sensors, and detects the supply volume of the electrically conductive solution (physiological saline) supplied from the supply source 6. A detection signal indicating a detection result of the supply volume can be transmitted to the control section 52 in a wired or wireless manner. The control section 52 controls the actuation state of the supply pump 12 on the basis of the detection result in the supply volume detection section 57. The supply volume detection section 57 may be provided in the supply source 6, and if small in size, may be provided inside the treatment instrument 2 in the supply path 13. That is, the supply volume has only to be detected before the spout of the electrically conductive solution from the spout 32.

A suction volume detection section 58 is attached to the drain tank 16 of the suction source 7. The suction volume detection section 58 is, for example, one of known liquid level sensors or water level sensors, and detects the suction volume of the electrically conductive solution (suctioned object) sucked by the suction source 7. A detection signal indicating a detection result of the suction volume can be transmitted to the control section 52 in a wired or wireless manner. The control section 52 controls the actuation state of the suction pump 17 on the basis of the detection result in the suction volume detection section 58. A known flow volume sensor may be used as the suction volume detection section 58, in which case the suction volume detection section 58 is provided in the suction path 18. If small in size, the suction volume detection section 58 may be provided inside the treatment instrument 2 in the suction path 18. That is, the suction volume of the electrically conductive solution has only to be detected after the suction of the electrically conductive solution from the suction hole 35.

As described above, the ID of the treatment instrument 2 to be connected may be read by the control section 52 of the processing unit 50. In this case, the storage section 51 stores information regarding the actuation characteristics of the supply pump 12, information regarding the actuation characteristics of the suction pump 17, ID information regarding the kinds of treatment instruments 2 different in specifications, information regarding the supply volume from the supply source 6 corresponding to each ID, and information regarding suction volume by the suction source 7 corresponding to each ID. On the basis of the read ID and the information stored in the storage section 51, in each of the ablation output mode and the coagulation output mode, the actuation state of the supply pump 12 and the actuation state of the suction pump 17 are controlled by the control section 52, and the supply volume from the supply source 6 and the suction volume by the suction source 7 are adjusted.

As shown in FIG. 2, a temperature detection section 61 is fixed to the distal surface 27 of the treatment portion 25. The temperature detection section 61 is a temperature sensor such as a thermocouple. In the present embodiment, the temperature detection section 61 is located between the first electrode portions (active electrodes) 46A and 46B and the second electrode portion (return electrode) 47. In the present embodiment, a first distance L1 from the temperature detection section 61 to the first electrode portion (one of 46A and 46B closer from the temperature detection section 61) is smaller than a second distance L2 from the temperature detection section 61 to the second electrode portion 47. Therefore, the temperature detection section 61 is located in the vicinity of the first electrode portions 46A and 46B. In the present embodiment, a plasma treatment control unit which controls the plasma treatment system 1 in a plasma treatment (low-temperature ablation treatment) is constituted by the energy source unit 3 (including the processing unit 50), the supply volume detection section 57, the suction volume detection section 58, and the temperature detection section 61.

As shown in FIG. 1, one end of a signal path 62 is connected to the temperature detection section 61. The signal path 62 extends through the inside of the treatment instrument 2 (through the inside of the probe 23) and through the inside of the cable 26, and has the other end connected to the control section 52 of the processing unit 50. The signal path 62 is formed by, for example, a signal wire extending through the inside of the probe 23 and a signal wire extending through the inside of the cable 26. The signal path 62 is separable at the connection position of the cable 26 to the holding case 21. A detection signal indicating the detection result in the temperature detection section 61 is transmitted to the control section 52 via the signal path 62.

The control section 52 of the processing unit 50 is configured to transmit a control signal to the temperature adjustment unit 8 in a wired or wireless manner, and configured to control the actuation state, for example, the heat generation state of the temperature adjustment unit 8. In the present embodiment, the temperature adjustment unit 8 is actuated to heat or cool the electrically conductive solution in the supply source 6, and adjust the temperature of the electrically conductive solution. The control section 52 controls the actuation state of the temperature adjustment unit 8 and adjusts the temperature of the electrically conductive solution in the supply source 6 on the basis of the detection result in the temperature detection section 61. The temperature of the electrically conductive solution in the vicinity of the temperature adjustment unit 8 changes in accordance with the change of the actuation state of the temperature adjustment unit 8. That is, the control section 52 controls the adjustment of the temperature of the electrically conductive solution in the temperature adjustment unit 8 on the basis of the detection result in the temperature detection section 61. The temperature adjustment unit 8 may adjust the temperature of the electrically conductive solution in the supply path 13, and if small in size, may adjust the temperature of the electrically conductive solution in the supply path 13 inside the treatment instrument 2. That is, the temperature of the electrically conductive solution has only to be adjusted by the temperature adjustment unit 8 before the spout of the electrically conductive solution from the spout 32. The detection of the temperature in the temperature detection section 61 and the control of the actuation state of the temperature adjustment unit 8 by the control section 52 in the treatment will be described in detail later.

Figure 3:
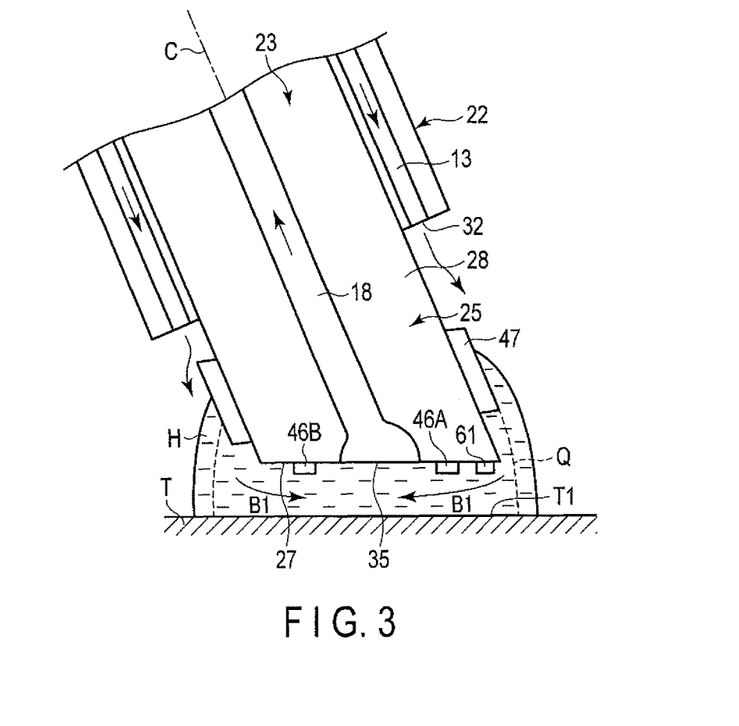
FIG. 3 is a schematic diagram showing a state at the time of a treatment in the vicinity of the treatment portion according to the first embodiment.

FIG. 3 is a diagram showing a state in the vicinity of the treatment portion 25 in a treatment (e.g., a treatment to ablate a treated target). The treatment shown in FIG. 3 is referred to as a low-temperature ablation treatment, and is used in, for example, the resection of a tonsil. As shown in FIG. 3, in a treatment to ablate a treated target T such as a living tissue, the distal surface 27 of the treatment portion 25 is put to face a surface T1 of the treated target T. The treatment portion 25 (the distal surface 27) is located apart from the treated target T without being in direct contact with the treated target T. Since the distal surface 27 is opposed to the surface T1 of the treated target T, the first electrode portions 46A and 46B are located closer to the treated target T than the second electrode portion 47. Thus, in the treatment, the first electrode portions 46A and 46B serve as electrodes that mainly act on the treated target T.

In the treatment, the supply pump 12 and the suction pump 17 are actuated, and the electrically conductive solution is supplied from the supply source 6 through the supply path 13. The supplied electrically conductive solution then spouts toward the surface T1 of the treatment target T from the spout 32 of the treatment portion 25. The electrically conductive solution that has spouted from the spout 32 is sucked by the suction source 7. The electrically conductive solution outside the treatment portion 25 is sucked from the suction hole 35 through the suction path 18, and collected in the drain tank 16. The electrically conductive solution is supplied by the supply source 6 and the sucked by the suction source 7 as described above, and a perfusion layer H of the electrically conductive solution is thereby formed between the treatment portion 25 and the surface T1 of the treated target T. In the perfusion layer H, a flow (an arrow B1 in FIG. 3) of the electrically conductive solution from the spout 32 toward the suction hole 35 is formed.

In the treatment, the first electrode portions 46A and 46B and the second electrode portion 47 are immersed in the perfusion layer H. The first electrode portions 46A and 46B and the second electrode portion 47 are located between the spout 32 and the suction hole 35, and are therefore located to be easily immersed in the perfusion layer H. By the supply of radio-frequency energy (radio-frequency electric power) to the first electrode portions 46A and 46B and the second electrode portion 47 in a state where the first electrode portions 46A and 46B and the second electrode portion 47 are immersed in the perfusion layer H, a radio-frequency current flows between the first electrode portions 46A and 46B and the second electrode portion 47 in the perfusion layer H. When the radio-frequency energy is output in the ablation output mode, a voltage (electric potential difference) between the first electrode portions 46A and 46B and the second electrode portion 47 increases. If the voltage between the first electrode portions 46A and 46B and the second electrode portion 47 increases, the radio-frequency current flows through the perfusion layer H of the electrically conductive solution, and a vapor layer is formed between the between the first electrode portions 46A and 46B and the second electrode portion 47 in the perfusion layer H. A breakdown occurs in the vapor layer, and plasma is generated in the perfusion layer H of the electrically conductive solution. That is, in the perfusion layer H, a plasma layer Q is formed in a region where the radio-frequency current flows between the first electrode portions 46A and 46B and the second electrode portion 47. The low-temperature ablation treatment in which a treated target such as a living tissue is ablated is conducted by the generated plasma.

The spout 32, the suction hole 35, the first electrode portions 46A and 46B, and the second electrode portion 47 in the treatment portion 25 are not limited in position, number, dimensions, and shape to the configuration in FIG. 2 and FIG. 3. For example, in a certain example, the supply path 13 extends through the inside of the probe 23, the spout 32 is provided on the distal surface 27 of the treatment portion 25, the suction path 18 extends through the space between the probe 23 and the sheath 22, and the suction hole is provided at the distal end of the space between the sheath 22 and the probe 23. In another certain example, both the supply path 13 and the suction path 18 extend through the inside of the probe 23, the spout 32 is located on the outer circumferential surface 28 of the treatment portion 25, and the suction hole 35 is located on the distal surface 27 of the treatment portion 25. In yet another certain example, both the first electrode portions (46A and 46B) and the second electrode portion (47) are fixed to the distal surface 27 of the treatment portion 25. Accordingly, the first electrode portion (46A and 46B) and the second electrode portion (47) have only to be located so that the first electrode portion (46A and 46B) and the second electrode portion (47) are disposed in the treatment portion 25 in a state to intervene between the spout 32 and the suction hole 35 and can be immersed in the perfusion layer H of the electrically conductive solution in which the flow from the spout 32 toward the suction hole 35 is formed.

Although the supply path 13 and the suction path 18 pass through the inside of the treatment instrument 2 in the present embodiment, it is not limited to this. For example, at least one of the supply path 13 and the suction path 18 may be provided separately from the treatment instrument 2. However, in this case as well, the first electrode portion (46A and 46B), the second electrode portion (47), and the temperature detection section 61 are fixed to the treatment portion 25, and located at positions to be immersed in the perfusion layer H.

A perfusion liquid volume (liquid volume) in the perfusion layer H has only to be such a volume (degree) that the first electrode portions 46A and 46B and the second electrode portion 47 are immersed in the perfusion layer H, and the perfusion liquid volume is preferably not extremely high. This effectively prevents the electrically conductive solution that has been ejected from the spout 32 from flowing into parts (e.g. the bronchi) other than the treated target T in the body without being sucked from the suction hole 35. This effectively prevents complications occurring due to the inflow of the electrically conductive solution used in the treatment and blood resulting from the treatment into parts other than the treatment target T. Here, even when the perfusion liquid volume in the perfusion layer H is the highest, the sheath 22, for example, is not immersed in the perfusion layer H.

The surface area of the second electrode portion 47 immersed in the perfusion layer H is preferably larger than the surface areas of the first electrode portions 46A and 46B immersed in the perfusion layer H. Therefore, in the perfusion layer H, the current density of the radio-frequency current is lower in the vicinity of the second electrode portion 47 than in the vicinity of the first electrode portions 46A and 46B, and the temperature of the perfusion layer H is lower in the vicinity of the second electrode portion 47 than in the vicinity of the first electrode portions 46A and 46B. Consequently, plasma is more easily generated in the vicinity of the first electrode portions 46A and 46B, and the first electrode portions 46A and 46B close to the treated target T appropriately function as active electrodes that greatly affect the treated target T. That is, the second electrode portion 47 far from the treated target T is effectively prevented from functioning as an active electrode, and the plasma layer Q appropriate for the treatment is formed in the perfusion layer H.

The treated target T ablated by the plasma is sucked from the suction hole 35 through the suction path 18 together with the electrically conductive solution in the perfusion layer H. The mechanism to ablate the treated target T by plasma has not been proved at the present stage. An OH radical generated in the plasma layer Q is considered to be one of the causes that ablate the treated target T at the present stage. The energy level of the radio-frequency energy necessary to generate plasma in the perfusion layer H (the voltage between the first electrode portions 46A and 46B and the second electrode portion 47, and the current value of the radio-frequency current flowing through the perfusion layer) changes depending on the structures (e.g., shapes, positions, and inter-electrode distances) of the first electrode portions 46A and 46B and the second electrode portion 47. Therefore, information regarding the structures of the first electrode portions 46A and 46B and the second electrode portion 47 and information regarding the energy level of the radio-frequency energy necessary to generate plasma are stored in the storage section 51, and the control section 52 may control the output state of the radio-frequency energy on the basis of the stored information.

Figure 4:
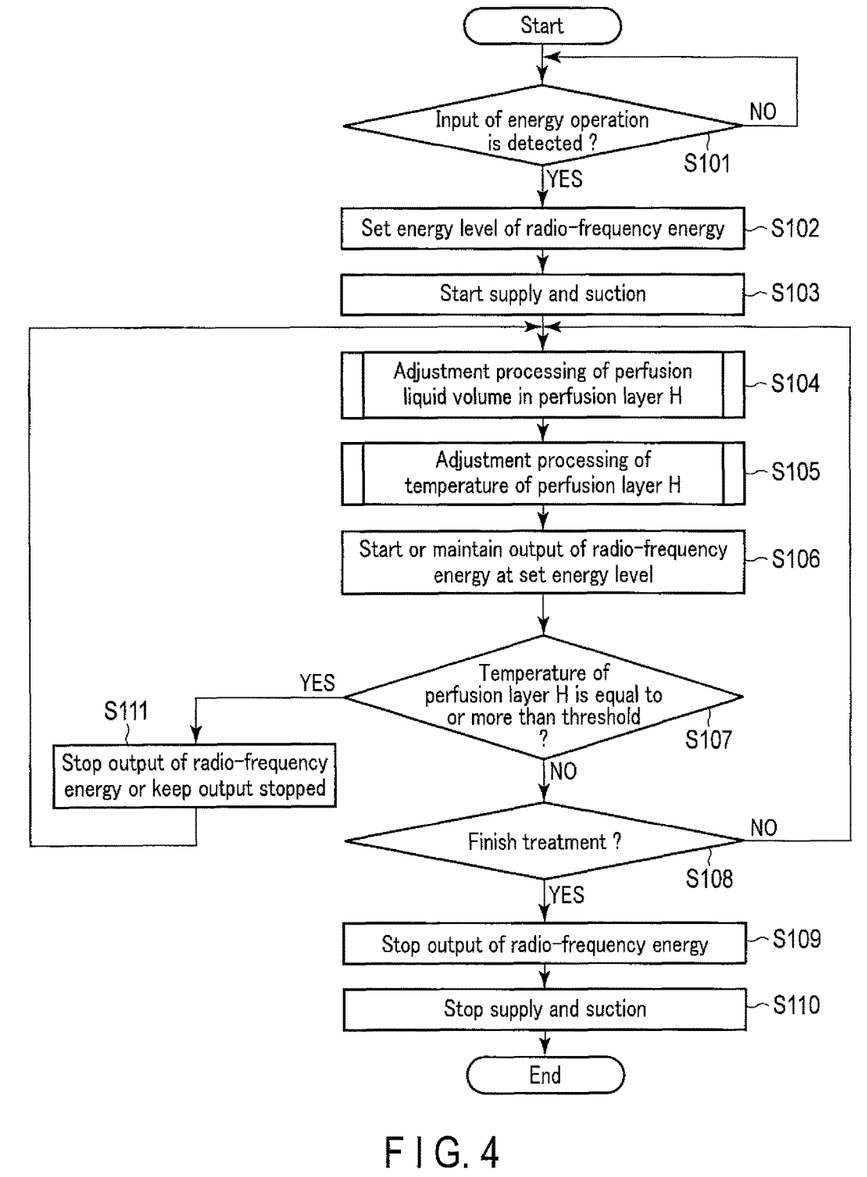
FIG. 4 is a flowchart showing processing in a treatment of a plasma treatment control unit according to the first embodiment.

FIG. 4 is a flowchart showing processing in the plasma treatment control unit (including the energy source unit 3 and the temperature detection section 61) in a treatment (mainly, a treatment to ablate the treated target T). In the treatment, an energy operation is input in the energy operation input section 5 in a state where the distal surface 27 of the treatment portion 25 faces the treated target T. For example, the first input switch 56A is turned on by the input of the energy operation. Accordingly, as shown in FIG. 4, an operation signal is input to the control section 52, and the input of the energy operation is detected by the control section 52 (step S101—Yes). On the basis of the input of the energy operation, the control section 52 sets the energy level of the radio-frequency energy (radio-frequency electric power) to be output from the radio-frequency energy source 41 (step S102). Here, the energy level to be set is determined on the basis of the specifications of the treatment instrument 2 used in the treatment (e.g., the positions, dimensions, and shapes of the first electrode portions 46A and 46B and the second electrode portion 47). A higher energy level is set in the ablation output mode than in the coagulation output mode. The information regarding the energy level to be set may be stored in the storage section 51.

On the basis of the control signal from the control section 52, the supply pump 12 is actuated, and the suction pump 17 is actuated. Accordingly, the supply of the electrically conductive solution from the supply source 6 and the suction by the suction source 7 are started (step S103). The control section 52 controls the actuation state of the supply pump 12 and the actuation state of the suction pump 17, for example, on the basis of the actuation characteristics of the supply pump 12 and the actuation characteristics of the suction pump 17 stored in the storage section 51. When the supply by the supply source 6 and the suction by the suction source 7 are started, the perfusion layer H of the electrically conductive solution is formed between the distal surface 27 of the treatment portion 25 and the treated target T as described above.

Adjustment processing of the perfusion liquid volume which is the liquid volume in the perfusion layer H is then performed (step S104). Adjustment processing of the temperature of the perfusion layer H is also performed (step S105). In the low-temperature ablation treatment, the generation state of plasma changes depending on the perfusion liquid volume in the perfusion layer H and the temperature of the electrically conductive solution in the perfusion layer H. That is, even when the output state of the radio-frequency energy does not change, the generation of plasma changes in accordance with the perfusion liquid volume and the temperature in the perfusion layer H. Thus, it is important to appropriately generate plasma in the perfusion layer H by adjusting the perfusion liquid volume and the temperature in the perfusion layer H to appropriate ranges (values).

Figure 5:
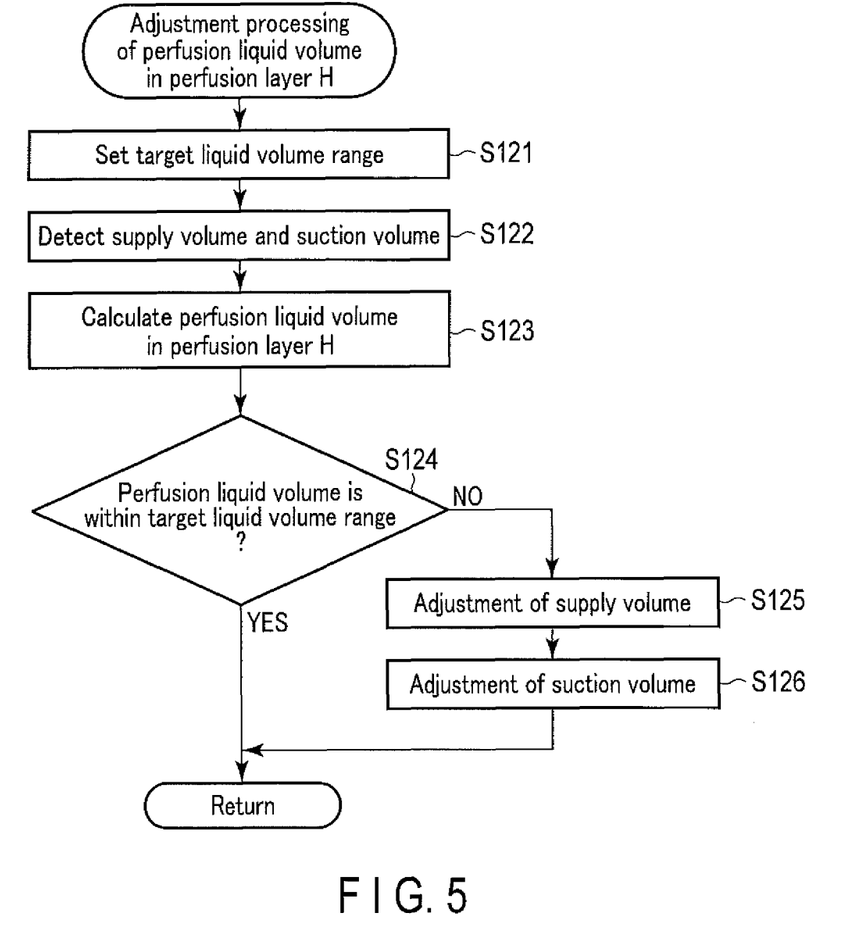
FIG. 5 is a flowchart showing processing to adjust a perfusion liquid volume in a perfusion layer in FIG. 4.

FIG. 5 is a flowchart showing processing to adjust the perfusion liquid volume in the perfusion layer H. As shown in FIG. 5, in the processing to adjust the perfusion liquid volume, a target liquid volume range (liquid volume value) of the perfusion liquid volume is first set by the target setting section 53 (step S121). The target liquid volume range is, for example, a liquid volume range in which appropriate plasma is generated in a treatment. The target liquid volume range is set, for example, on the basis of the specifications of the treatment instrument 2 (e.g., the shapes and sizes of the first electrode portions 46A and 46B and the second electrode portion 47). The target liquid volume range may be set on the basis of the presence of an output of radio-frequency energy, and when radio-frequency energy is being output, the target liquid volume range may be set on the basis of the output state of the radio-frequency energy (e.g., the energy level set in step S102). In this case, for example, a table indicating the relation between the specifications of the treatment instrument 2 and the target liquid volume range and the relation between the output state of the radio-frequency energy and the target liquid volume range are previously stored in the storage section 51. The target liquid volume range is a liquid volume range suited to a treatment, so that the liquid volume range is set to a state where the first electrode portions 46A and 46B and the second electrode portion 47 are immersed in the perfusion layer H even at the minimum level in the liquid volume range. Even when the perfusion liquid volume is the maximum in the liquid volume range, the inflow of the electrically conductive solution into parts other than the treated target T in the body is prevented, and the sheath 22, for example, is not immersed in the perfusion layer H.

The supply volume of the electrically conductive solution from the supply source 6 is then detected by the supply volume detection section 57, and the suction volume of the electrically conductive solution sucked by the suction source 7 (including the ablated treated target T) is detected by the suction volume detection section 58 (step S122). A detection signal indicating the supply volume and the detection signal indicating the suction volume are then transmitted to the control section 52. The arithmetic processing section 55 then calculates the perfusion liquid volume in the perfusion layer H on the basis of the detection result of the supply volume and a detection result of the suction volume (step S123). The perfusion liquid volume is calculated by the use of, for example, a calculation program stored in the storage section 51.

The control section 52 then judges whether the perfusion liquid volume in the perfusion layer H is within the target liquid volume range set in step S121 (step S124). When the perfusion liquid volume in the perfusion layer H calculated in step S123 is within the target liquid volume range (step S124—Yes), the supply pump 12 and the suction pump 17 are controlled by the control section 52 to a state in which the perfusion liquid volume is maintained. In contrast, when the perfusion liquid volume in the perfusion layer H is not within the target liquid volume range (step S124—No), the supply volume from the supply source 6 is adjusted by the supply pump 12 (step S125), and the suction volume to the suction source 7 is adjusted by the suction pump 17 (step S126). In this instance, the control section 52 controls the actuation state of the supply pump 12 and the actuation state of the suction pump 17 on the basis of the detection result of the supply volume, the detection result of the suction volume, and the calculation result of the perfusion liquid volume. The supply volume and the suction volume are adjusted to a state where the perfusion liquid volume will be within the target liquid volume range set in step S121. For example, when the perfusion liquid volume is smaller than the target liquid volume range, the control section 52 controls the actuation state of the supply pump 12 to increase the supply volume, and the control section 52 controls the actuation state of the suction pump 17 to reduce the suction volume.

Figure 6:
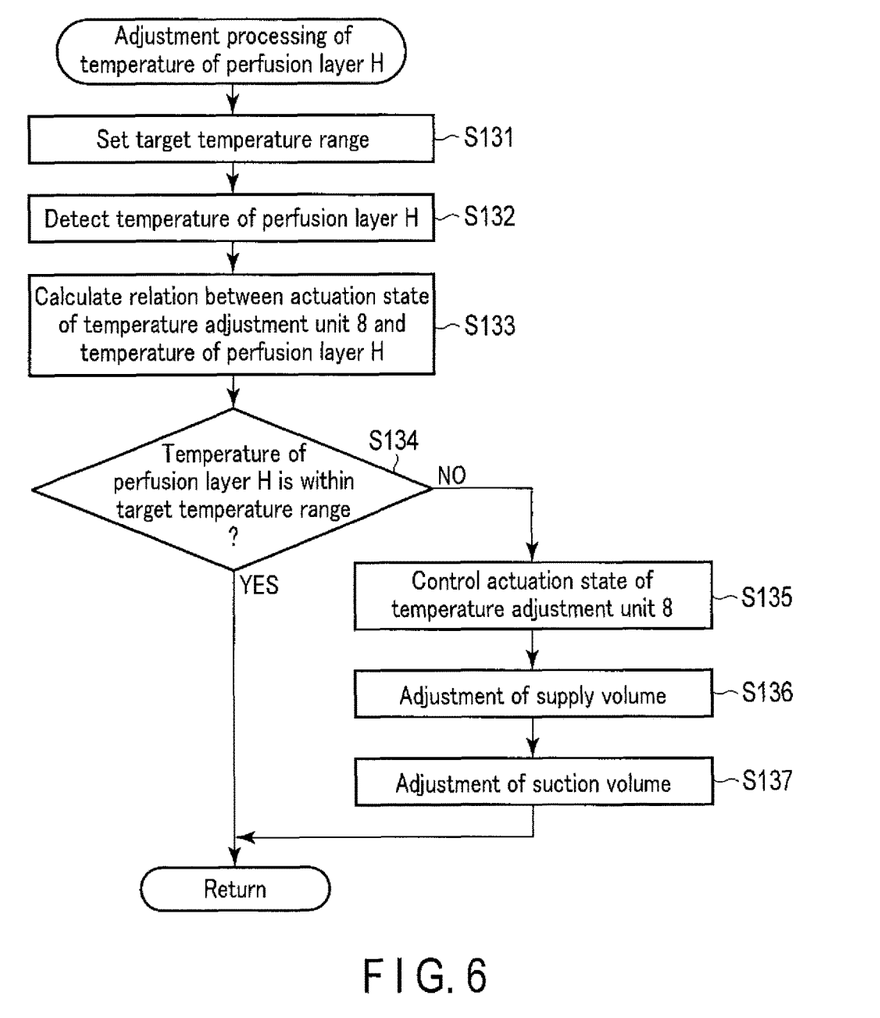
FIG. 6 is a flowchart showing processing to adjust the temperature of the perfusion layer in FIG. 4.

FIG. 6 is a flowchart showing processing to adjust the temperature of the perfusion layer H. As shown in FIG. 6, in the processing to adjust the temperature of the perfusion layer, a target temperature range (temperature) of the perfusion layer is first set by the target setting section 53 (step S131). The target temperature range is, for example, a temperature range in which appropriate plasma is generated in a treatment. The target temperature range is set, for example, on the basis of the specifications of the treatment instrument 2 and the presence of an output of radio-frequency energy. When radio-frequency energy is being output, the target temperature range may be set on the basis of the output state of the radio-frequency energy (e.g., the energy level set in step S102). In this case, for example, a table indicating the relation between the specifications of the treatment instrument 2 and the target temperature range and the relation between the output state of the radio-frequency energy and the target temperature range are stored in the storage section 51. The target temperature range may be set on the basis of the perfusion liquid volume in the perfusion layer H calculated in step S123. In general, in the low-temperature ablation treatment, the temperature of the perfusion layer H reaches 45° C. to 90° C., and is preferably 60° C. to 70° C. Therefore, the minimum value in the target temperature range is 45° C. or more, and is preferably 60° C. or more. The maximum value in the target temperature range is 90° C. or less, and is preferably 70° C. or less.

The temperature of the perfusion layer H is then detected by the temperature detection section 61 (step S132). As shown in FIG. 3, the temperature detection section 61 is disposed between the spout 32 and the suction hole 35, and located at a position to be immersed in the perfusion layer H in a state where the first electrode portions 46A and 46B and the second electrode portion 47 are immersed in the perfusion layer H. Thus, the temperature of the perfusion layer H formed between the treated target T and the treatment portion 25 in the low-temperature ablation treatment is appropriately detected. Although the temperature detection section 61 is fixed to the distal surface 27 of the treatment portion 25 in the present embodiment, it is not limited to this. For example, the temperature detection section 61 may be disposed on the outer circumferential surface 28 of the treatment portion 25 on the condition that the temperature detection section 61 is located at a position to be immersed in the perfusion layer H in a state where the first electrode portions 46A and 46B and the second electrode portion 47 are immersed in the perfusion layer H. That is, the position of the temperature detection section 61 is not limited if the temperature detection section 61 is located at a position to be immersed in the perfusion layer H in a state where the first electrode portions 46A and 46B and the second electrode portion 47 are immersed in the perfusion layer H.

In the present embodiment, the temperature detection section 61 is located between the first electrode portions (active electrodes) 46A and 46B and the second electrode portion (return electrode) 47. That is, the temperature detection section 61 is located in a region where the radio-frequency current flows through the perfusion layer H between the first electrode portions 46A and 46B and the second electrode portion 47 in a state where the first electrode portions 46A and 46B and the second electrode portion 47 are immersed in the perfusion layer H. Thus, in the low-temperature ablation treatment, the temperature of the region where the plasma layer Q that acts on the treated target T is generated is detected by the temperature detection section 61. In the present embodiment, the first distance L1 from the temperature detection section 61 to the first electrode portion (one of 46A and 46B closer from the temperature detection section 61) is smaller than the second distance L2 from the temperature detection section 61 to the second electrode portion 47. Thus, in the low-temperature ablation treatment, the temperature detection section 61 is located in the vicinity of the first electrode portions (active electrodes) 46A and 46B that greatly affect the treated target T. Therefore, the temperature of the region that greatly affect the treatment target T in the perfusion layer H is detected by the temperature detection section 61.

If the temperature of the perfusion layer H is detected (step S132), the relation between the actuation state of the temperature adjustment unit 8 (i.e., the adjustment state of the temperature of the electrically conductive solution by the temperature adjustment unit 8) and the temperature of the perfusion layer H is calculated by the arithmetic processing section 55 (step S133). For example, the change of the temperature of the perfusion layer H relative to the heat generation state or cooling state in the temperature adjustment unit 8 is calculated. The relation between the actuation state of the temperature adjustment unit 8 and the temperature of the perfusion layer H changes in accordance with, for example, the supply volume from the supply source 6, the supply speed (liquid supply speed), the length (dimensions) of the supply path 13, and the position of the temperature adjustment unit 8. Thus, for example, the speed of supply from the supply source 6 may be calculated on the basis of the supply volume detected in step S122, and the relation between the actuation state of the temperature adjustment unit 8 and the temperature of the perfusion layer H may be calculated on the basis of the detected supply volume and the calculated supply speed. For example, information regarding the length of the supply path 13 and the specifications of the supply pump 12 may be stored in the storage section 51, and the relation between the actuation state of the temperature adjustment unit 8 and the temperature of the perfusion layer H may be calculated on the basis of the stored information.

The control section 52 then judges whether the temperature of the perfusion layer H is within the target temperature range set in step S131 (step S134). When the temperature of the perfusion layer H detected in step S132 is within the target temperature range (step S134—Yes), the temperature adjustment unit 8 is controlled by the control section 52 to a state in which the temperature of the perfusion layer H is maintained. In contrast, when the temperature of the perfusion layer H is not within the target temperature range (step S134—No), the actuation state (e.g., the heat generation state) of the temperature adjustment unit 8 is controlled by the control section 52 on the basis of the detection result of the temperature of the perfusion layer H (step S135). The actuation state of the temperature adjustment unit 8 is controlled by using the relation between the actuation state of the temperature adjustment unit 8 and the temperature of the perfusion layer H calculated in step S133. As a result, the heat generation amount in the temperature adjustment unit 8, for example, is adjusted. When the electrically conductive solution is not only heated but also cooled by the temperature adjustment unit 8, it is possible to adjust not only the heat generation amount but also the cooling amount of the temperature adjustment unit 8 by controlling the actuation state of the temperature adjustment unit 8. The actuation state of the temperature adjustment unit 8 is controlled (i.e., the temperature of the electrically conductive solution is adjusted before the spout 32) so that the temperature of the perfusion layer H is within the target temperature range set in step S131. For example, when the temperature of the perfusion layer H is lower than the target temperature range, the heat generation amount in the temperature adjustment unit 8 is increased by controlling the actuation state of the temperature adjustment unit 8.

As shown in FIG. 6, the control section 52 controls the actuation state of the supply pump 12 and controls the actuation state of the suction pump 17 in addition to the temperature adjustment unit 8 on the basis of the detection result of the temperature of the perfusion layer H. Accordingly, the supply volume (supply speed) of the electrically conductive solution supplied through the supply path 13 is adjusted (step S136), and the suction volume (suction speed) of the electrically conductive solution (including the ablated treated target) suctioned through the suction path 18 is adjusted (step S137). The temperature of the perfusion layer H is adjusted by controlling the supply volume and the suction volume. In this instance, the perfusion liquid volume in the perfusion layer H may change or may not change by the adjustment of the supply volume and the suction volume. In the present embodiment, the perfusion liquid volume in the perfusion layer H is adjusted to the target liquid volume range in step S104, so that it is preferable that the perfusion liquid volume in the perfusion layer H do not change in steps S136 and S137. The supply volume and the suction volume are adjusted so that the temperature of the perfusion layer H is within the target temperature range set in step S131. For example, when the temperature of the perfusion layer H is higher than the target temperature range and when the temperature of the electrically conductive solution is lower in the vicinity of the temperature adjustment unit 8 than in the perfusion layer H, the supply volume (supply speed) from the supply source 6 and the suction volume (suction speed) to the suction source 7 are increased. As a result, the low-temperature electrically conductive solution is rapidly supplied to the perfusion layer H, and the temperature of the perfusion layer H decreases. In this instance, both supply volume and the suction volume are increased so that it is possible to change the temperature of the perfusion layer H without changing the perfusion liquid volume in the perfusion layer H.

If the adjustment processing of the perfusion liquid volume (step S104) and the adjustment processing of the temperature of the perfusion layer H (step S105) are performed, the output of the radio-frequency energy from the radio-frequency energy source 41 is started at the energy level set in step S102 (step S106). The perfusion liquid volume and the temperature in the perfusion layer H are set to the appropriate ranges in the low-temperature ablation treatment in steps S104 and S105. Thus, plasma is appropriately generated in the perfusion layer H as described above by the supply of the radio-frequency energy output to the first electrode portions 46A and 46B and the second electrode portion 47.

In the energy source unit 3, a threshold which is a value higher than the target temperature range is set by the control section 52, or stored in the storage section 51. If the radio-frequency energy is output, the temperature of the perfusion layer H is detected by the temperature detection section 61, and the control section 52 judges whether or not the detected temperature of the perfusion layer H is equal to or more than the threshold (step S107). When the temperature of the perfusion layer H is equal to or more than the threshold (step S107—Yes), the output of the radio-frequency energy from the radio-frequency energy source 41 is stopped (step S111). If the radio-frequency energy is output at the energy level in the ablation output mode in the case where the temperature of the perfusion layer H is equal to or more than the threshold, there is a possibility that, for example, the treated target and living tissues other than the treated target may be thermally damaged.

When the treatment is carried on (step S108—No), the adjustment processing of the perfusion liquid volume (step S104) and the adjustment processing of the temperature of the perfusion layer H (step S105) are performed, and the output of the radio-frequency energy is maintained in step S106. A judgment in step S107 is then made. That is, even in a state where radio-frequency energy is being output at the energy level in the ablation output mode, the adjustment processing of the perfusion liquid volume (step S104) and the adjustment processing of the temperature of the perfusion layer H (step S105) are performed, and the judgment in step S107 is made. When the temperature of the perfusion layer H is equal to or more than the threshold (step S107—Yes), the output of the radio-frequency energy is stopped as described above (step S111). That is, in step S111, the presence of an output of radio-frequency energy from the radio-frequency energy source 41 and the output state of the radio-frequency energy are controlled by the control section 52 on the basis of the calculation result of the perfusion liquid volume and the detection result of the temperature of the perfusion layer H.

In step S111, the output of the radio-frequency energy may not be stopped but the radio-frequency energy may be output at an energy level lower than the set energy level instead. In this case, the radio-frequency energy is output at a low energy level, so that the voltage between the first electrode portions 46A and 46B and the second electrode portion 47 is lower, and no plasma is generated in the perfusion layer H regardless of the perfusion liquid volume and the temperature in the perfusion layer H. Whether or not the temperature of the perfusion layer H is equal to or more than the threshold may be judged in step S107 in a state where the output of the radio-frequency energy is stopped. In this case, if the temperature of the perfusion layer H is equal to or more than the threshold, the output of the radio-frequency energy is kept stopped. In a certain example, the adjustment processing of the temperature of the perfusion layer H (step S105) may be only performed, and the adjustment processing of the perfusion liquid volume in the perfusion layer H (step S104) may not be performed. A program to perform the processing shown in FIG. 4 to FIG. 6 may be stored in the storage section 51.

In the present embodiment described above, the perfusion liquid volume in the perfusion layer H is calculated from the detected supply volume and suction volume, and the supply volume and the suction volume are adjusted so that the perfusion liquid volume in the perfusion layer H will be within the target liquid volume range. Thus, if the target liquid volume range is set to a liquid volume range appropriate for a treatment, plasma is appropriately generated in the perfusion layer H and treatment performance is ensured in the low-temperature ablation treatment.

In the present embodiment, the temperature of the perfusion layer H is detected by the temperature detection section 61, and on the basis of the detection result of the temperature of the perfusion layer H, the actuation state (e.g., the heat generation state and the cooling state) of the temperature adjustment unit 8 is controlled so that the temperature of the perfusion layer H will be within the target temperature range. Thus, if the target temperature range is set to a temperature range appropriate for a treatment, plasma is appropriately generated in the perfusion layer H and treatment performance is ensured in the low-temperature ablation treatment.

(Modifications)

Figure 7:
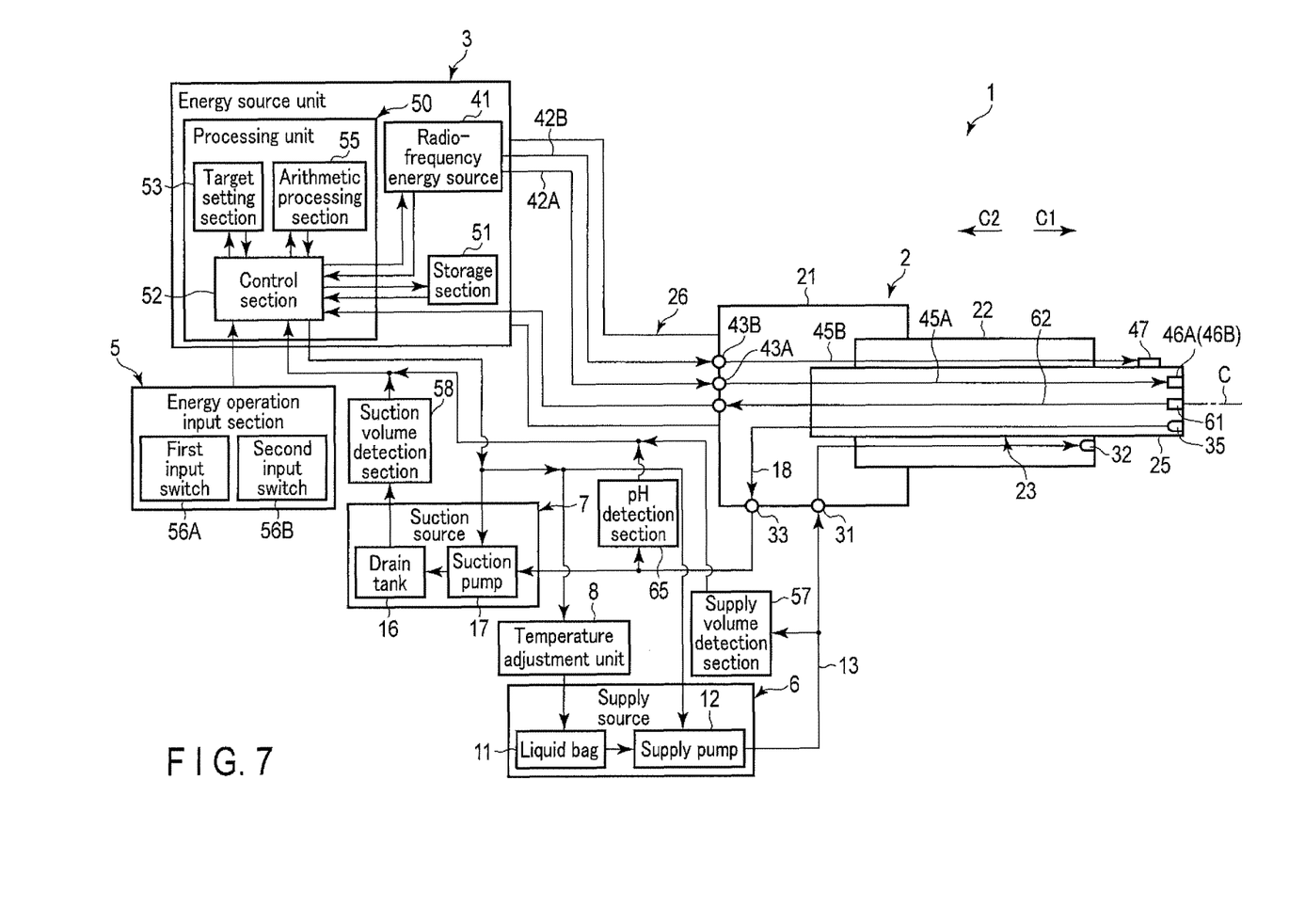
FIG. 7 is a schematic diagram showing a plasma treatment system according to a certain modification.

As shown in FIG. 7, in a certain modification, a pH detection section 65 is provided in the suction path 18. In the present modification, the pH detection section is located outside the treatment instrument 2. The pH detection section 65 is, for example, a pH sensor which detects pH of the electrically conductive solution by passing an electric current through the electrically conductive solution (including the ablated treatment target) in the suction path 18. A detection signal based on the detection result of pH of the electrically conductive solution is transmitted to the control section 52 in a wired or wireless manner. In the present modification, a plasma treatment control unit which controls the plasma treatment system 1 in the plasma treatment (low-temperature ablation treatment) is constituted by the pH detection section 65 in addition to the energy source unit 3 (including the processing unit 50), the supply volume detection section 57, the suction volume detection section 58, and the temperature detection section 61.

The pH detection section 65 may be provided in the suction source 7, and if small in size, may be provided inside the treatment instrument 2 in the suction path 18. That is, pH of the electrically conductive solution has only to be detected by the pH detection section 65 after the suction of the electrically conductive solution from the suction hole 35.

Before the spout of the electrically conductive solution from the spout 32 of the supply path 13, pH of the electrically conductive solution is within a predetermined range. For example, when the electrically conductive solution is a physiological saline, pH is within a range of 4.5 to 7.0. The ablated treated target is included in the electrically conductive solution by the low-temperature ablation treatment, so that pH of the electrically conductive solution changes, and pH is no loner within the predetermined range. Therefore, if pH of the electrically conductive solution is detected after the suction of the electrically conductive solution from the suction hole 35, whether the treated target T is appropriately ablated, that is, whether plasma is appropriately generated in the perfusion layer H can be judged. pH of the electrically conductive solution to be detected changes depending on, for example, whether a treated target is included, the kind of treated target, and the content of the treated target.

In the present modification, the control section 52 controls the actuation state of the temperature adjustment unit 8 and adjusts the temperature of the perfusion layer H on the basis of the detection result of pH in the pH detection section 65 in addition to the detection result of the temperature of the perfusion layer H in the temperature detection section 61. The supply volume from the supply source 6 and the suction volume to the suction source 7 may be adjusted and the perfusion liquid volume in the perfusion layer H may be adjusted on the basis of the detection result in the pH detection section 65 in addition to the detection result in the temperature detection section 61. The adjustment of the perfusion liquid volume and the adjustment of the temperature of the perfusion layer H are performed as in the first embodiment.

In the plasma treatment control unit and the plasma treatment system (1) according to the embodiment and others described above, the temperature detection section (61) which is configured to detect the temperature of the perfusion layer (H) is fixed to the treatment portion (25), and is located at a position to be immersed in the perfusion layer (H) in a state where the first electrode portions (46A and 46B) and the second electrode portion (47) are immersed in the perfusion layer (H). On the basis of the detection result in the temperature detection section (61), the control section (52) controls the adjustment of the temperature in the temperature adjustment unit (8) and controls the supply volume and suction volume of the electrically conductive solution so that the temperature of the perfusion layer (H) is within the target temperature range.

Characteristic matters are additionally noted below.

Notes (Additional Note 1)

A plasma treatment control unit provided in a plasma treatment system which is provided with a treatment portion including a first electrode portion, and a second electrode portion provided in a state where the position thereof relative to the first electrode portion does not change, wherein an electrically conductive solution that has spouted from a spout of a supply path is sucked from a suction hole of a suction path so that a perfusion layer of the electrically conductive solution from the spout toward the suction hole is formed, the temperature of the electrically conductive solution is adjusted by a temperature adjustment unit before the spout of the electrically conductive solution from the spout, plasma is generated in the perfusion layer by the supply of radio-frequency energy to the first electrode portion and the second electrode portion in a state where the first electrode portion and the second electrode portion are immersed in the perfusion layer, and the plasma is used to treat a treated target, the plasma treatment control unit comprising:

a temperature detection section fixed to the treatment portion, the temperature detection section being located at a position to be immersed in the perfusion layer in a state where the first electrode portion and the second electrode portion are immersed in the perfusion layer, and being configured to detect the temperature of the perfusion layer; and a control section which is configured to control the actuation state of the temperature adjustment unit and control a supply volume of the electrically conductive solution supplied through the supply path and a suction volume of the electrically conductive solution sucked through the suction path on the basis of a detection result in the temperature detection section so that the temperature of the perfusion layer is within a target temperature range.

(Additional Note 2)

A plasma treatment system comprising:

the plasma treatment control unit according to Additional note 1;

a treatment instrument including the treatment portion to which the temperature detection section is fixed; and a temperature adjustment unit which is configured to adjust the temperature of the electrically conductive solution before the spout of the electrically conductive solution from the spout.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A plasma treatment system comprising:

a supply source;

a supply path in which a spout configured to spout an electrically conductive solution is formed, and which is configured to supply the electrically conductive solution from the supply source toward the spout;

a suction path in which a suction hole configured to suck the electrically conductive solution is formed, and which is configured to suck the electrically conductive solution to form a perfusion layer of the electrically conductive solution from the spout toward the suction hole;

a treatment portion including a first electrode portion and a second electrode portion which is provided in a state where a position thereof relative to the first electrode portion does not change, the treatment portion being configured to generate plasma in the perfusion layer by a supply of radio-frequency energy to the first electrode portion and the second electrode portion in a state of immersing these electrode portions in the perfusion layer, thereby treating a target;

a radio-frequency energy source configured to output the radio-frequency energy which is supplied to the first electrode portion and the second electrode portion;

a temperature adjustment unit which is located on a supply source side with respect to the spout, and a temperature of the electrically conductive solution in a vicinity of the temperature adjustment unit being configured to change in accordance with an actuation state of the temperature adjustment unit;

a temperature detection section which is fixed to the treatment portion, and which is located at a position to be immersed in the perfusion layer in the state where the first electrode portion and the second electrode portion are immersed in the perfusion layer, whereby a temperature of the perfusion layer is detected in the state of immersing the electrode portions in the perfusion layer;

a control section which is configured to control the actuation state of the temperature adjustment unit on the basis of a detection result by the temperature detection section so as to adjust the temperature of the electrically conductive solution in the vicinity of the temperature adjustment unit, and being configured to control a supply volume of the electrically conductive solution supplied through the supply path and a suction volume of the electrically conductive solution sucked through the suction path on the basis of the detection result in the temperature detection section, thereby maintaining the temperature of the perfusion layer within a target temperature range, wherein the control section is configured to control a presence of an output of the radio-frequency energy from the radio-frequency energy source and an output state of the radio-frequency energy on the basis of the detection result of the temperature of the perfusion layer; a target setting section which is configured to set the target temperature range of the perfusion layer; a supply volume detection section which is configured to detect the supply volume of the electrically conductive solution supplied through the supply path; a suction volume detection section which is configured to detect the suction volume through the suction path regarding the electrically conductive solution that has spouted from the spout; and an arithmetic processing section which is configured to calculate a perfusion liquid volume of the electrically conductive solution in the perfusion layer on the basis of a detection result in the supply volume detection section and a detection result in the suction volume detection section, wherein the target setting section is configured to set the target temperature range on the basis of the calculated perfusion liquid volume.

2. The plasma treatment system according to claim 1, wherein the target setting section is configured to set the target temperature range on the basis of a presence of an output of the radio-frequency energy from the radio-frequency energy source or on the basis of the output state of the radio-frequency energy.

3. The plasma treatment system according to claim 1, wherein the control section is configured to adjust the supply volume through the supply path and the suction volume through the suction path on the basis of the calculated perfusion liquid volume.

4. The plasma treatment system according to claim 1, wherein the control section is configured to set a threshold which is a value higher than the target temperature range, and configured to stop the output of the radio-frequency energy from the radio-frequency energy source when the detected temperature of the perfusion layer is equal to or more than the threshold.

5. The plasma treatment system according to claim 1, wherein the control section is configured to control the supply volume and the suction volume of the electrically conductive solution to adjust the temperature of the electrically conductive solution in the perfusion layer without changing the perfusion liquid volume in the perfusion layer.

6. The plasma treatment system according to claim 1, wherein the arithmetic processing section is configured to calculate a relation between the actuation state of the temperature adjustment unit and the temperature of the perfusion layer, wherein the control section is configured to control the actuation state of the temperature adjustment unit on the basis of the relation calculated by the arithmetic processing section.

7. The plasma treatment system according to claim 6, wherein the arithmetic processing section is configured to calculate the relation between the actuation state of the temperature adjustment unit and the temperature of the perfusion layer on the basis of the detection result in the supply volume detection section.

8. The plasma treatment system according to claim 1, wherein
the temperature detection section is fixed to the treatment portion in a region where the radio-frequency current flows through the perfusion layer between the first electrode portion and
the second electrode portion in the state where the first electrode portion and the second electrode portion are immersed in the perfusion layer.

9. The plasma treatment system according to claim 8, wherein
the first electrode portion is located closer to the target than the second electrode portion in the state where the first electrode portion and the second electrode portion are immersed in the perfusion layer, and
a first distance from the temperature detection section to the first electrode portion is smaller than a second distance from the temperature detection section to the second electrode portion.

10. The plasma treatment system according to claim 1, further comprising
a suction source which is configured to collect the electrically conductive solution sucked through the suction path; and
a pH detection section which is located on a suction source side with respect to the suction hole, and which is configured to detect pH of the electrically conductive solution in a vicinity of the pH detection section, wherein
the control section is configured to control the actuation state of the temperature adjustment unit and configured to control the supply volume and the suction volume of the electrically conductive solution on the basis of a detection result in the pH detection section in addition to the detection result in the temperature detection section.

11. The plasma treatment system according to claim 1, wherein
the first electrode portion is located on a distal side with respect to the second electrode portion in the treatment portion, and
the temperature detection section is located on the distal side with respect to the second electrode portion in the treatment portion.

12. A plasma treatment system comprising:
a supply source;
a supply path connected to a spout that is configured to supply an electrically conductive solution, the supply path being configured to supply the electrically conductive solution from the supply source toward the spout;
a suction path connected to a suction hole that is configured to transport the electrically conductive solution, and the suction path being configured to transport the electrically conductive solution that forms a perfusion layer from the spout toward the suction hole;
a treatment portion including: (A) a first electrode portion, and (B) a second electrode portion that has a fixed position to the first electrode portion, the treatment portion being configured to generate plasma in the perfusion layer by supplying radio-frequency energy to the first electrode portion and the second electrode portion when the first and second electrode portions are immersed in the perfusion layer, thereby treating a target;
a radio-frequency energy source configured to output the radio-frequency energy supplied to the first electrode portion and the second electrode portion;
a temperature adjustment unit disposed on a supply source side with respect to the spout, the temperature adjustment unit controlling a temperature of the electrically conductive solution in a vicinity of the temperature adjustment unit in response to an actuation state of the temperature adjustment unit;
a temperature sensor fixed to the treatment portion, the temperature sensor being immersed in the perfusion layer in the state when the first electrode portion and the second electrode portion are immersed in the perfusion layer, the temperature sensor being configured to measure a temperature of the perfusion layer when the electrode portions are immersed in the perfusion layer;
a processor programmed to:
receive a detection result of the temperature of the perfusion layer from the temperature sensor;
control the actuation state of the temperature adjustment unit based on the detection result such that the temperature of the electrically conductive solution is adjusted in the vicinity of the temperature adjustment unit;
control a supply volume of the electrically conductive solution supplied through the supply path and a suction volume of the electrically conductive solution transported through the suction path based on the detection result, thereby maintaining the temperature of the perfusion layer within a target temperature range, and
control the output of the radio-frequency energy from the radio-frequency energy source and an output state of the radio-frequency energy based on the detection result; a target setting section which is configured to set the target temperature range of the perfusion layer; a supply volume detection section which is configured to detect the supply volume of the electrically conductive solution supplied through the supply path; a suction volume detection section which is configured to detect the suction volume through the suction path regarding the electrically conductive solution that has spouted from the spout; and an arithmetic processing section which is configured to calculate a perfusion liquid volume of the electrically conductive solution in the perfusion layer on the basis of a detection result in the supply volume detection section and a detection result in the suction volume detection section, wherein the target setting section is configured to set the target temperature range on the basis of the calculated perfusion liquid volume.

\* \* \* \* \*